United States Patent
Cau

(10) Patent No.: US 11,324,532 B2
(45) Date of Patent: May 10, 2022

(54) ROBOTIC MANIPULATOR INTERFACE FOR HINGED SURGICAL TOOLS

(71) Applicant: MICROSURE B.V., Son (NL)

(72) Inventor: Raimondo Cau, Helmond (NL)

(73) Assignee: MICROSURE B.V., Son (NL)

( * ) Notice: Subject to any disclaimer, the term of this patent is extended or adjusted under 35 U.S.C. 154(b) by 70 days.

(21) Appl. No.: 16/486,034

(22) PCT Filed: Feb. 15, 2018

(86) PCT No.: PCT/EP2018/053800
§ 371 (c)(1),
(2) Date: Aug. 14, 2019

(87) PCT Pub. No.: WO2018/149924
PCT Pub. Date: Aug. 23, 2018

(65) Prior Publication Data
US 2020/0046394 A1   Feb. 13, 2020

(30) Foreign Application Priority Data

Feb. 16, 2017 (EP) .................................... 17156469

(51) Int. Cl.
*A61B 17/3201* (2006.01)
*A61B 17/30* (2006.01)
(Continued)

(52) U.S. Cl.
CPC .......... *A61B 17/3201* (2013.01); *A61B 17/28* (2013.01); *A61B 17/30* (2013.01);
(Continued)

(58) Field of Classification Search
CPC ..... A61B 17/3201; A61B 34/70; A61B 46/10; A61B 17/28; A61B 17/30; A61B 2017/00477; A61B 90/50
See application file for complete search history.

(56) References Cited

U.S. PATENT DOCUMENTS 6,436,107 B1 * 8/2002 Wang ................. A61B 1/00149
318/568.11
8,746,252 B2 * 6/2014 McGrogan ................ H01F 5/02
128/852
(Continued)

FOREIGN PATENT DOCUMENTS

DE     102013002813 A1    8/2014
EP        1931275 A1    6/2008
(Continued)

OTHER PUBLICATIONS

International Search Report and Written Opinion for PCT Patent App. No. PCT/EP2018/053800 (dated Mar. 28, 2018).
(Continued)

*Primary Examiner* — Julian W Woo
(74) *Attorney, Agent, or Firm* — McCoy Russell LLP

(57) ABSTRACT

Some embodiments are directed to a robotic manipulator interface for coupling a hinged surgical tool to a manipulator of a surgical robot, the interface including a first interface member to be coupled to the manipulator, and a second interface member to be coupled to the first interface member, the second interface member being arranged to mount the hinged surgical tool, wherein the first interface member includes a pinching mechanism for pinching the hinged surgical tool when the second interface member is coupled to the first interface member, wherein the pinching mechanism includes two movable protrusions protruding from a surface of the first interface member, the first interface member including a built-in actuating mechanism for moving the protrusions to each other to push two arms of the mounted hinged surgical tool towards each other so as to actuate the mounted hinged surgical tool through the sterile drape.

15 Claims, 9 Drawing Sheets

(51) Int. Cl.
*A61B 34/00* (2016.01)
*A61B 46/10* (2016.01)
*A61B 17/28* (2006.01)
*A61B 17/00* (2006.01)

(52) U.S. Cl.
CPC .............. *A61B 34/70* (2016.02); *A61B 46/10* (2016.02); *A61B 2017/00477* (2013.01)

(56) References Cited

U.S. PATENT DOCUMENTS

| | | | |
|---|---|---|---|
| 9,259,277 B2* | 2/2016 | Rogers | A61B 90/50 |
| 10,004,563 B2* | 6/2018 | Gombert | B25J 19/0075 |
| 10,736,707 B2* | 8/2020 | Pennoyer | A61B 34/35 |
| 2004/0135388 A1 | 7/2004 | Sgobero et al. | |
| 2011/0087238 A1 | 4/2011 | Wang et al. | |
| 2021/0015578 A1* | 1/2021 | Marchese | A61B 34/70 |

FOREIGN PATENT DOCUMENTS

| | | |
|---|---|---|
| EP | 2981226 A1 | 2/2016 |
| EP | 3097863 A1 | 11/2016 |
| WO | WO2007/041094 A1 | 4/2007 |
| WO | WO2007/143859 A1 | 12/2007 |
| WO | WO2014/162217 A1 | 10/2014 |

OTHER PUBLICATIONS

International Preliminary Report on Patentability for PCT Patent App. No. PCT/EP2018/053800 (dated Mar. 29, 2019).

\* cited by examiner

ROBOTIC MANIPULATOR INTERFACE FOR HINGED SURGICAL TOOLS

CROSS REFERENCE TO RELATED APPLICATIONS

This application is a national phase filing under 35 C.F.R. § 371 of and claims priority to PCT Patent Application No. PCT/EP2018/053800, filed on Feb. 15, 2018, which claims the priority benefit under 35 U.S.C. § 119 of European Patent Application No. 171556469.3, filed on Feb. 16, 2017, the contents of each of which are hereby incorporated in their entireties by reference.

BACKGROUND

The presently disclosed subject matter relates to a robotic manipulator interface for coupling a hinged surgical tool to a manipulator of a surgical robot. The presently disclosed subject matter particularly relates to coupling of ordinary hinged surgical tools commonly used by surgeons, such as forceps, scissors or other hinged surgical tools.

Nowadays many surgeries are performed by surgical robots. These surgical robots may include so-called manipulators which generally have an end effector which handles a surgical tool acting upon the patient. Since surgical robotic manipulators are difficult and may be impossible to sterilize as a whole, the manipulator is typically contained within a sterile drape, while the surgical instrument, which may be sterilized, is held by the manipulator through the sterile drape.

For example, EP1931275 describes a robotic surgical system which includes a manipulator arm, a surgical accessory clamp for coupling a surgical accessory to a distal end portion of the manipulator arm, and a sterile drape covering the accessory clamp and the manipulator arm to shield the accessory clamp and the manipulator arm from the sterile field. A specific example is described with reference to FIGS. 9 and 10. Here, a robotic surgical manipulator is shown which includes a surgical accessory clamp which holds a surgical accessory, with the sterile drape being arranged in between the surgical accessory clamp and the surgical accessory.

This solution works well for rigid surgical tools like cannulas or scalpels, or for robotic surgical tools designed to be intrinsically compatible with the robotic surgical manipulator, but cannot be used for normal handheld hinged surgical tools like forceps.

US 20040135388 describes a gripper for tweezers which includes a case to be mounted on a robot arm which encloses a tweezers fixing and indexing device and a device for actuating the arms of the tweezers which includes a motor member which actuates pushers acting on the arms of the tweezer.

EP3097863 describes a remote controlled flexible instrument having a disposable component. The disposable component can be engaged into and disengaged from a non-disposable, reusable base. The components can be locked onto the base by snapping or interlocking matched parts.

SUMMARY

An aspect of the presently disclosed subject matter is to provide a robotic manipulator interface for coupling a hinged surgical tool to a manipulator of a surgical robot wherein the manipulator can be covered by a sterile drape while still being able to manipulate the hinged surgical tool.

A first aspect of the presently disclosed subject matter provides a robotic manipulator interface for coupling a hinged surgical tool to a manipulator of a surgical robot, the interface including a first interface member to be coupled to the manipulator, and a second interface member to be coupled to the first interface member, the second interface member being arranged to mount the hinged surgical tool, wherein the first interface member includes a pinching mechanism for pinching the hinged surgical tool when the second interface member is coupled to the first interface member.

In accordance with the above measures, the robotic manipulator is, at least in use, covered by a sterile drape so as to separate the manipulator from the sterile world in which the surgery takes place. The hinged surgical tool is not covered by the drape, but can still be activated by the pinching mechanism that is arranged in the first interface member which, at least in use, is fully covered by the drape.

Unlike in the related art, the surgical tool is not held by a (first) interface member from within the sterile drape but rather by a (second) interface member which is located outside the sterile drape. It has been found that holding a hinged surgical tool from within the sterile drape increases the chance of rupturing or otherwise damaging the sterile drape. Namely, in this case, not only the 'pinching' force is applied to the hinged surgical tool via the sterile drape, but also any force involved in holding the hinged surgical tool. By holding the hinged surgical tool from outside of the sterile drape with a further interface member, this latter force is not applied via the sterile drape anymore but rather entirely outside of the sterile drape. Accordingly, the chance of rupturing or otherwise damaging the sterile drape is reduced.

Optionally, the robotic manipulator interface further includes couplers for coupling the second interface member to the first interface member. The couplers may include one or more magnetic elements arranged in at least one of the first interface member and the second interface member. In this way a sterile drape can easily be placed in between, while having a coupling between the two members. No further arrangement, mechanical or otherwise, is needed.

Optionally, the couplers includes a clamping arrangement for clamping the second interface member onto the first member. The drape may be placed around the first member and then the second member may be coupled to the first member by a clamping arrangement, such as an elastic band, a tape, a string, a tie-wrap, a ring or a plurality of one of the above.

Optionally, the pinching mechanism includes two movable protrusions protruding from a surface of the first interface member, the first interface member including a built-in actuating mechanism for moving the protrusions to each other so as to push two arms of the hinged surgical tool towards each other.

Optionally, each of the protrusions includes a rounded top. In this way the risk of damage to the drape is minimized.

Optionally, the surface of the first interface member is substantially flat. Such a surface will increase the contact surface between the first and second interface member, while at the same time avoiding damage to the drape. For example, the surface may include an at least 80%, 90% or 95% flat surface area.

Optionally, the first interface member includes a disc shaped part and one or multiple elongated parts extending from a front surface of the disc shaped part, wherein the elongated part includes a flat surface lying in a plane parallel to a main axis of the disc shaped part. Such a configuration enables the mounting of surgical tools in the second interface member while allowing a precise positioning relative to a rotational axis of the first interface member.

Optionally, the first interface member is rotatable around the main axis of the disc shaped part when coupled to the manipulator.

Optionally, the second interface member includes a substantially semi-cylindrical body. This will enable easy coupling by for example a ring to the first interface member.

Optionally, the substantially semi-cylindrical body has a middle section with a cross section that is smaller than a cross section at the outer ends of the body. The smaller cross section results in a groove in which coupling members can be arranged, in a way that they will stay in place during use.

Optionally, the second interface member includes a longitudinal cavity to accommodate at least part of the hinged surgical tool, wherein the second interface member includes an exit of the cavity at an outer end. The surgical tool can be mounted in the cavity and can stick out from the outer end. The second interface member can be designed so that the tool is aligned with the top surface of the first interface member, and aligned relative to the pinching mechanism.

Optionally, the second interface member includes a mounting element perpendicularly positioned relative to a main axis of the cavity, the mounting element including a hole for insertion of an outer end of the hinged surgical tool. In this way rear-hinged surgical tools can easily be positioned in the second interface member. The mounting element may be a plate or a block having a hole for insertion of the outer end of the hinged surgical tool. Alternatively, the mounting element may be a suitably formed thread. For front hinged surgical tools the mounting element can be a plate which is placed in line with the main axis of the cavity.

Optionally, the mounting element is flexible and/or resiliently arranged in the second interface member. In this way, positioning and fixation of the hinged surgical tool in the second interface member is done in a controlled manner.

Optionally, the second interface member includes an alignment element to be at least partly inserted in between two arms of the hinged surgical tool, near a pivoting point of the arms so as to align the hinged surgical tool relative to the second interface member.

Optionally, the first and second interface member includes aligners for aligning the second interface member relative to the first interface member.

A good alignment of the second interface member with respect to the first interface member will result in precise alignment of the tool relative to the manipulator.

A second aspect of the presently disclosed subject matter relates to a surgical robot including a robotic manipulator interface as described above.

A third aspect of the presently disclosed subject matter relates to a second interface member for use in a robotic manipulator interface as described above.

BRIEF DESCRIPTION OF THE DRAWINGS

These and other aspects of the presently disclosed subject matter are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
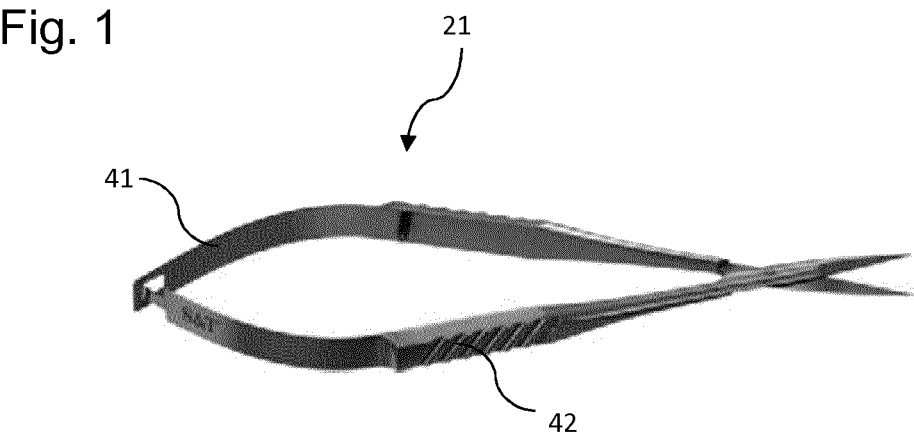
FIG. 1 shows a state of the art straight tip scissors with a flat handle and a leaf-spring end.
Figure 2:
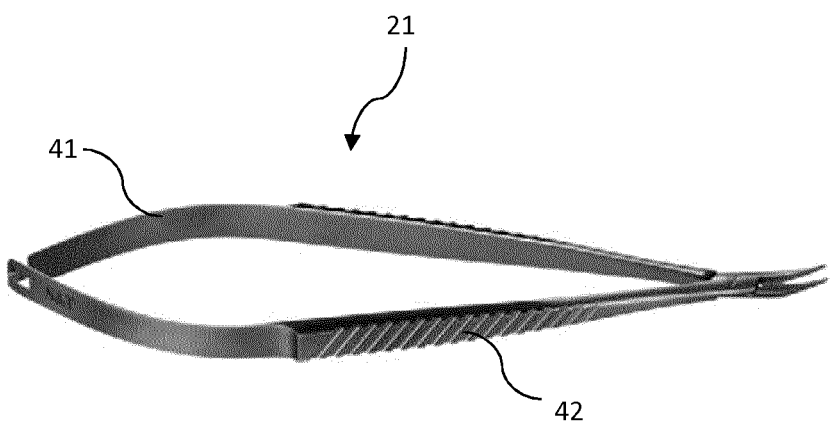
FIG. 2 shows a further example of a front-hinged surgical tool, being a curved tip needle holder with a flat handle and a leaf-spring end.
Figure 3:
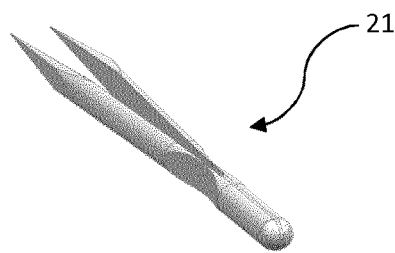
FIG. 3 shows a perspective view of a state of the art straight tip forceps.

The presently disclosed subject matter is particularly suitable for coupling of ordinary handheld hinged surgical tools, commonly used by surgeons, to a manipulator arm of a robot. FIGS. 1-3 show examples of such ordinary hinged surgical tools.

FIG. 1 shows a straight tip scissors 21 with a flat handle and a leaf-spring end. The scissors 21 include two arms which are hinged at the front side, i.e. at the side where the scissors make contact with a patient. FIG. 2 shows a further example of a front-hinged surgical tool, being a curved tip needle holder with a flat handle and a leaf-spring end.

Figure 4:
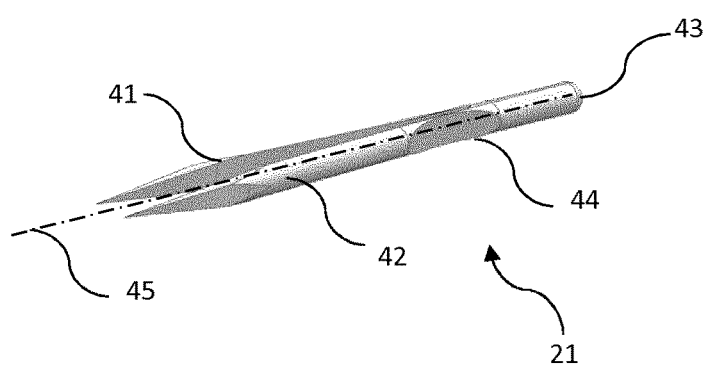
FIG. 4 shows a perspective view of the straight tip forceps of FIG. 3 from a different angle.

FIG. 3 shows a perspective view of a state of the art straight tip forceps 21, which is an example of a rear-hinged surgical tool. FIG. 4 shows a perspective view of the straight tip forceps 21 of FIG. 3 from a different angle. The forceps 21 includes a first arm 41 and a second arm 41. The forceps 21 includes a rounded end 43 and a rounded handle 44. Reference number 45 indicates a main axis of the tool.

According to an aspect a robotic manipulator interface is provided for coupling a hinged surgical tool to a manipulator of a surgical robot. The manipulator interface includes a first interface member configured to be coupled to the manipulator, and a second interface member configured to be coupled to the first interface member. The second interface member is arranged to mount the hinged surgical tool, while the first interface member includes a pinching mechanism for pinching the hinged surgical tool when the second interface member is coupled to the first interface member.

Figure 5:
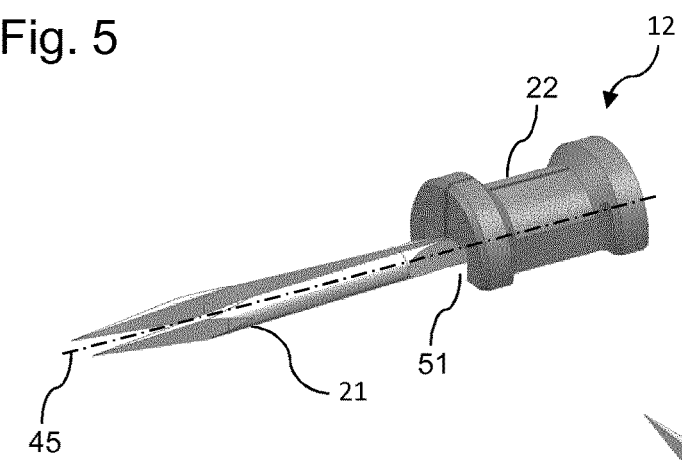
FIG. 5 shows a perspective view of a second interface member into which the forceps is mounted.

FIG. 5 shows a perspective view of a second interface member 12 into which the forceps 21 is mounted. In this embodiment, the interface member 12 includes a 3D body 22 having the shape of substantially cylindrical body cut in two. The 3D body has a relatively thin middle section and two larger end sections. The interface member 22 includes a cavity 51 in which part of the forceps are contained. A main axis of the cavity 51 in the 3D body 22 coincides with a main axis 45 of the forceps 21. In this embodiment, the cavity 51 is beam shaped, but it is noted that the shape of the cavity can be different as long as it provides sufficient space for the forceps to be operated without obstruction.

Figure 6:
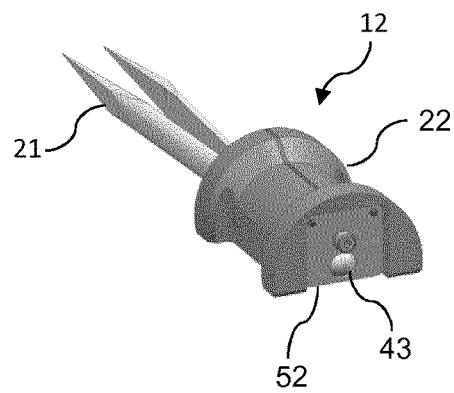
FIG. 6 shows another perspective view of the second interface member of FIG. 5 into which the forceps are/is mounted.

FIG. 6 shows another perspective view of the second interface member 12 of FIG. 5 into which the forceps 21 are/is mounted. FIG. 6 shows the back side of the second interface member 12. The second interface member 12 includes a mounting element 52 which includes a hole 53 (see also FIGS. 11a-11c) for inserting the rounded end 43 of the forceps 21. In this example, the mounting element 52 is a plate, for example made out of metal. By inserting the end 43 of the forceps 21 into the hole 53, the forceps 21 are fixed to the mounting element 52 and thus to the second interface member 12. Once the second interface member 12 is clamped onto the first interface member 11, the forceps 21 are coupled to the robotic manipulator.

Figure 7:
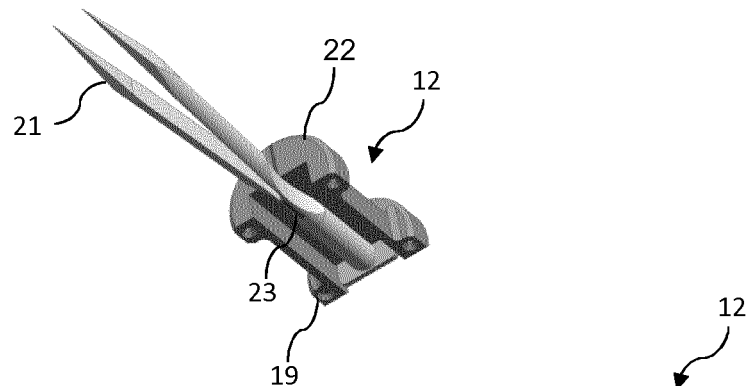
FIG. 7 shows a perspective view of the bottom of the second interface member of FIG. 5 into which the forceps are/is mounted.

FIG. 7 shows a perspective view of the bottom of the second interface member 12 of FIG. 5 into which the forceps 21 are/is mounted.

Figure 8:
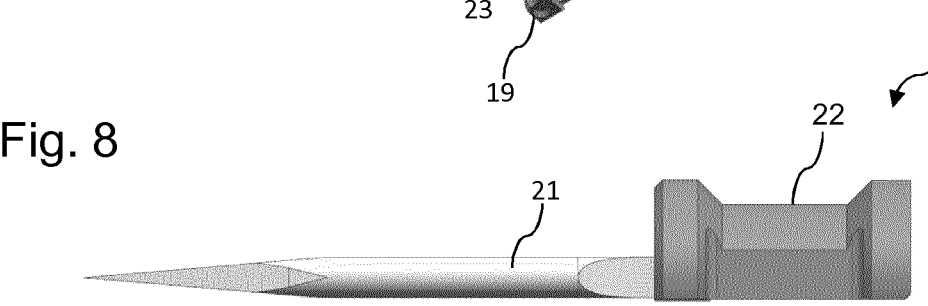
FIG. 8 shows a side view of the second interface member of FIG. 5 into which the forceps are/is mounted.

FIG. 8 shows a side view of the second interface member 12 of FIG. 5 into which the forceps 21 are/is mounted.

Figure 9:
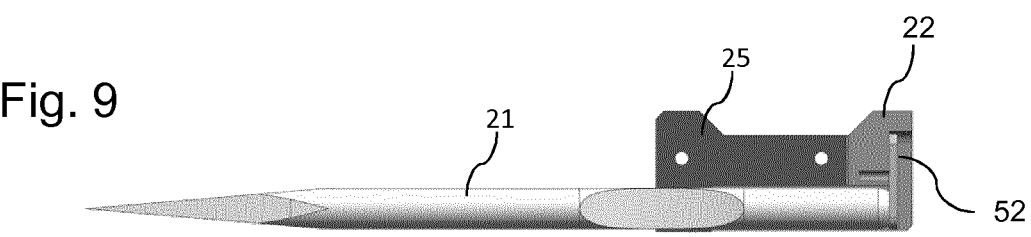
FIG. 9 shows a cut out view of FIG. 8 to show an embodiment of an alignment element arranged inside the second interface member.

FIG. 9 shows a cut out view of FIG. 8 to show an alignment element 25 arranged inside the second interface member 12. The alignment element 25 is used to align the forceps 21 with the main axis of the cavity 51 of the second interface member 12.

Figure 10:
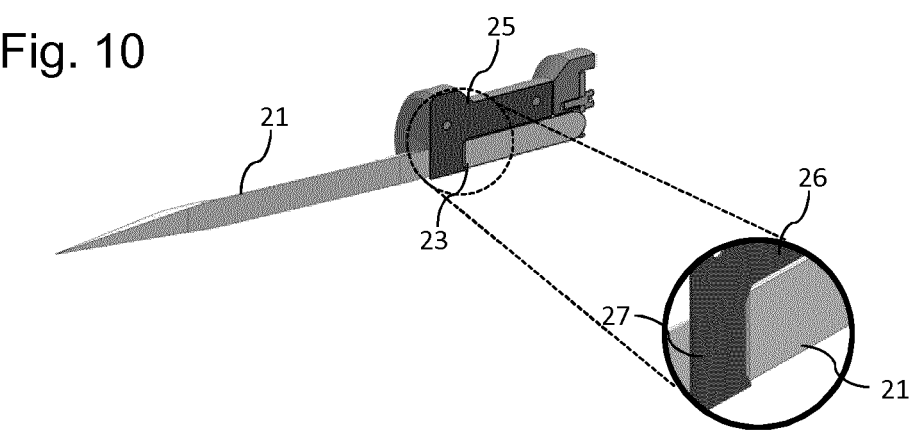
FIG. 10 shows a perspective view of FIG. 9 in which the forceps are cut out as well.

FIG. 10 shows a perspective view of FIG. 9 in which the forceps 21 are cut out as well. As can be seen in FIG. 10, the alignment element 25 is substantially L-shaped with a main part 26 coupled to the 3D body 22 of the interface member 12, and an extension 27 extending towards the bottom (in use towards the first interface member 11). When coupling the forceps 21, the extension of the alignment element 25 is placed between the two arms of the forceps 21 near the hinge of the forceps 21. On the right side of FIG. 10 an enlargement of a part of the cross section is shown. The extension 27 of the alignment element contains a v-groove, indicated by a dashed line in FIG. 11A. The angled edges of the v-groove come in contact with the top and bottom edge of the hinge of the forceps 21. In this way, the forceps 21 is centered with the v-groove, and thus properly aligned with the interface member 12. The mounting element 52 presses the hinge of the forceps against the v-groove. Any rotation of the forceps is prohibited by the hole in the mounting element 52, which partially envelopes the rounded rear end of the forceps 21. In this way, the orientation of the forceps 21 with respect to the interface member 12 is properly aligned and rigidly fixed.

The second interface member 22 with the mounting element 52 and the alignment element 25 arranged in the 3D-body, can be designed so as to create an interface able to hold and actuate a plethora of similar microsurgical tools.

It is noted that a lot of such microsurgical tools are hinged either at the front or at the rear end of the tool. Furthermore, most microsurgical tools have a longitudinal axis of symmetry. Rotation of the instrument around this axis is important movement during microsurgery. In straight tip instruments, the tip is aligned with the longitudinal axis to enable precise tip control. In curved or angled tip instruments, the tip is at an offset from this axis to provide improved accessibility.

A lot of microsurgical tools are spring-loaded, such that in a passive state the tool jaws are fully opened and in an actuated state the tool jaws are closed. These types of microsurgical tools can be actuated by symmetrically pressing the two handles inward It is noted that conventional microsurgical tools are designed to be held by hand, and therefore lack a dedicated reference point or plane for mounting to another structure. In the embodiment of FIGS. 5-10, a hinge point 23 of the surgical tool 21, see FIG. 7, is used in combination with the alignment element 25, see FIG. 10. The hinge point 23 may be mechanically preloaded against the alignment element 25 by the mounting element 52 also referred to as preload element 52.

The alignment element 25 and the preload element 52 are both connected to a 3D body 22. The alignment element 25 is rigidly connected to the 3D body 22. The preload element 52 may be elastically coupled to the 3D body 22, either by its own internal elasticity (e.g. bending elasticity) or by an external elastic element (e.g. a coil spring).

To cope with the large variety of conventional microsurgical instruments, the 3D body 22 can be equipped with different alignment elements 25 and corresponding preload elements 52, each tailored to a specific type or set of conventional surgical tools.

Figure 11:
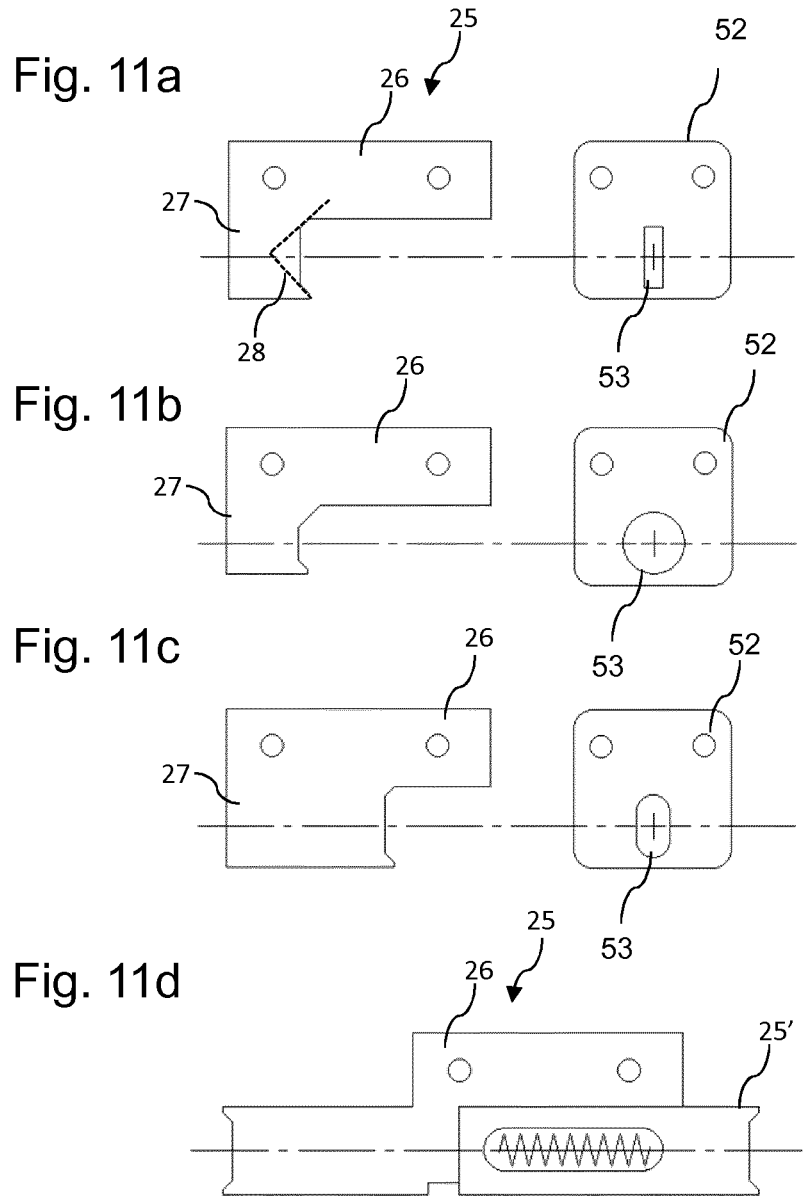
FIGS. 11*a*-11*c* show different embodiments of the alignment elements and corresponding mounting elements.
FIG. 11*d* shows an embodiment of the alignment element having a biased element.

FIGS. 11a-11c show different embodiments of the alignment elements 25 and corresponding preload elements 52. FIG. 11d shows an embodiment of the alignment element 25 having a biased element 25' to create a force towards the hinge point 23 of the surgical tool 21. As such, the embodiments in FIGS. 11a-11c are meant for rear hinged surgical tools, and the embodiments in FIG. 11d is suitable for front hinged surgical tools, such as shown in FIGS. 1 and 2. The advantage of the discussed embodiments is that different hinged surgical tools (with different lengths, manipulators, or type of actuation) can be contained by the same 3D body 22, by using the appropriate alignment elements 25 and corresponding preload elements 52. The elements 25 and 52 are relatively easy to produce and can be interchanged quickly and without deep technical knowledge and skills. The interface between the 3D body 22 and the interface member 11 is not influenced by the type of surgical tool used, which means that, in terms of safety and reliability, the interfacing functionality is never or rarely compromised.

As mentioned above, the preload element 52 contains a shaped surface, opening or hole 53 having a surface, edge or inner wall that matches with a surface on the rear end of the surgical tool 21. The alignment element 25 may have a v-groove, emphasized by the dashed lines 28 in FIG. 11a, which v-groove is pressed against the hinge 23 and as such the v-groove is aligned along the surgical tool's longitudinal axis of symmetry 45, see also FIG. 4. Similarly, an edge of the hole 53 on the preload element 52 is pressed against the surface of the tool 21, whereas the shape of the edge makes it align with the surgical tool's longitudinal axis of symmetry 45.

In an embodiment, the 3D body 22 has a bottom surface that is located at a distance and parallel to the surgical tool's longitudinal axis of symmetry 45. The distance and parallelism with respect to the axis of symmetry 45 can be well-defined by accurate alignment of the alignment element 25 and preload element 52 to the 3D body 22. This can be done e.g. by using dowel pins and holes, reference edges, or an additional alignment mechanism between.

Figure 12:
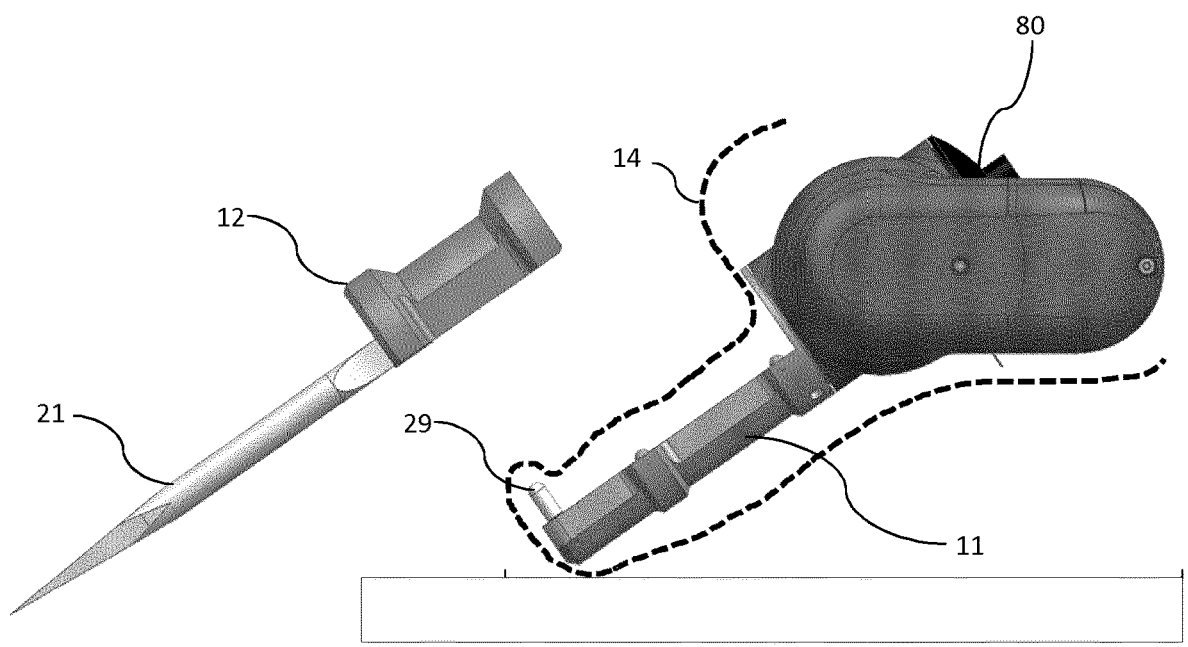
FIG. 12 schematically shows a side view of the first interface member coupled to a part of a robotic manipulator, and the second interface member coupled to the surgical tool.

FIG. 12 schematically shows a side view of an embodiment of the first interface member 11 rotatably coupled to an end part 80 of a robotic manipulator. Two protrusions 29 are arranged on the first interface member 11 which will be discussed in more detail below. The surgical tool 21 is coupled to a second interface member 12

A drape 14 is indicated by a dashed line to show how the end part of the manipulator 80 is separated from the sterile world. It is noted that, once the second interface member 12 is clamped onto the first interface member 11, the cross section of the drape 14 will have a different shape as compared to the shape shown in FIG. 12. It should be clear that the drape 14 can easily be placed between the first interface member 11 and the second interface member 12 before the second interface member 12 is clamped onto the first interface member 11 by the clamping arrangement (not shown in FIG. 12). The sterile drape 14 is placed around the first interface member 11 leaving the second interface member 12 uncovered. The drape 14 will separate the sterile world from the non-sterile world in which the robotic manipulator is located. Since the second interface member 12 is in the sterile world, it will have to be sterilized before use. The second interface member 12 may be a disposable module, or it may be a sterilizable module made of, for example, plastic, metal or ceramics.

It is noted that the surgical tool 20 is held by the second interface member 12, so not clamped between the two members as was the case in the related art. In this way the contact surfaces of the two interface members 11, 12 can be designed to minimize the risk of damage to the intermediate drape 14. In the embodiment of FIG. 12, the first interface member 11 is a substantially beam shaped element having a substantially flat contact surface. A specially designed drape including a sock can easily be positioned around the first interface member 11, after which the second interface member 12 can be coupled to the first interface member 11.

Figure 13A:
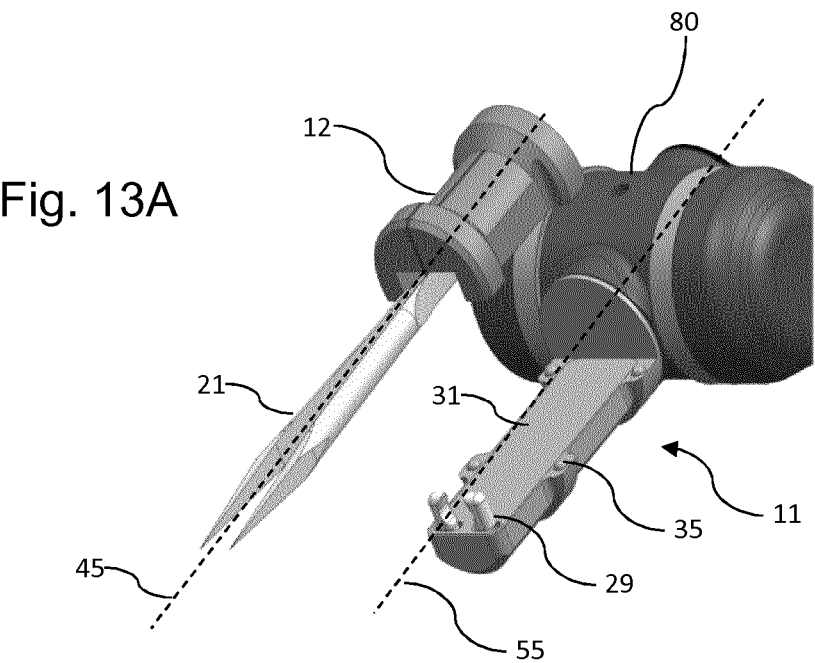
FIG. 13A is a perspective view of the modules of FIG. 12.

FIG. 13A is a perspective view of the modules of FIG. 12. The first interface member 11 has a substantially flat top surface 31 that is, at least after clamping, at a distance and parallel to the longitudinal axis 45 of the tool 21. The distance and parallelism with respect to the longitudinal axis 45 can be well defined. The distance may be selected so that there is no or little friction between the arms 41, 42 of the tool 21 and the drape 14 when the arms 41, 42 are moved by the protrusions 29.

In this embodiment a number of reference spheres 35 are arranged on the top surface 31 to cooperate with cavities 19 in the 3D body 22. In this way the second interface member 12 can be aligned with the first interface member 11 when clamping the members onto each other wherein the reference spheres 35 are placed into the cavities 19. In doing so, the surgical tool's axis of symmetry 45 is aligned with a rotation axis 55 of the first interface member 11. Instead of reference spheres and cavities on and in the contact surfaces, other types of aligners can be used such as alignment edges or ribs in or on the contact surface of the interface members.

In the embodiment of FIGS. 12 and 13A the 3D body 22 of the second interface member 12 has a cylindrical outer surface, the centerline of which is aligned with the surgical tool's longitudinal axis of symmetry 45. The advantage of having the alignment between the outer surface of the interface member 12 with the axis of symmetry 45 is that, when the interface member 12 is mounted, the whole assembly is axisymmetric around the axis 55. This leads to better weight distribution and thus better performance of the entire manipulator.

Figure 13B:
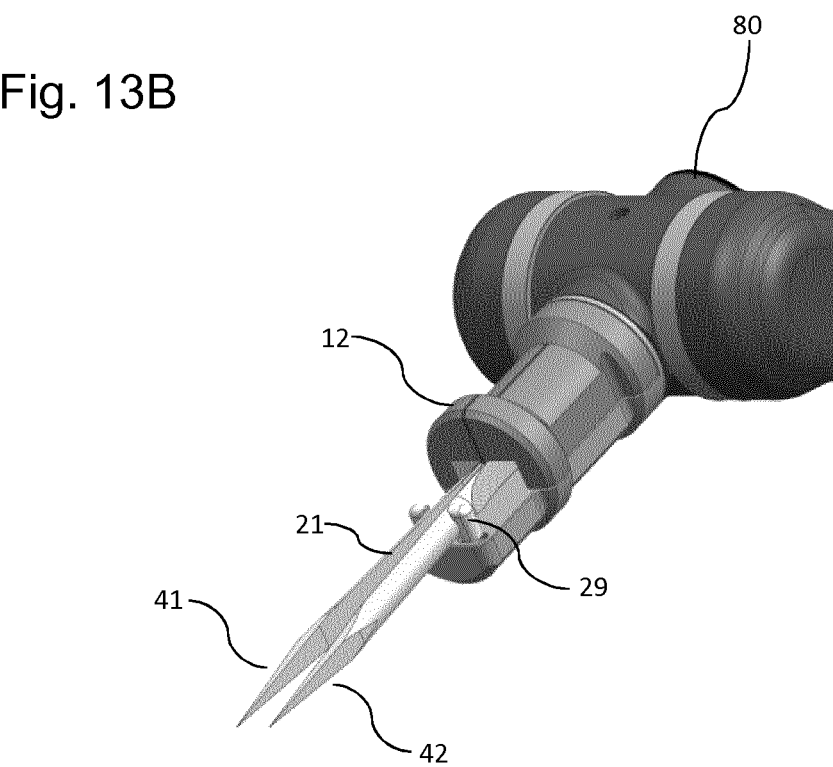
FIG. 13B is a perspective view of the interface and part of the manipulator after mounting.

FIG. 13B is a perspective view of the interface members and the manipulator 80 after mounting. The clamping arrangement and the drape are not shown.

Figure 14:
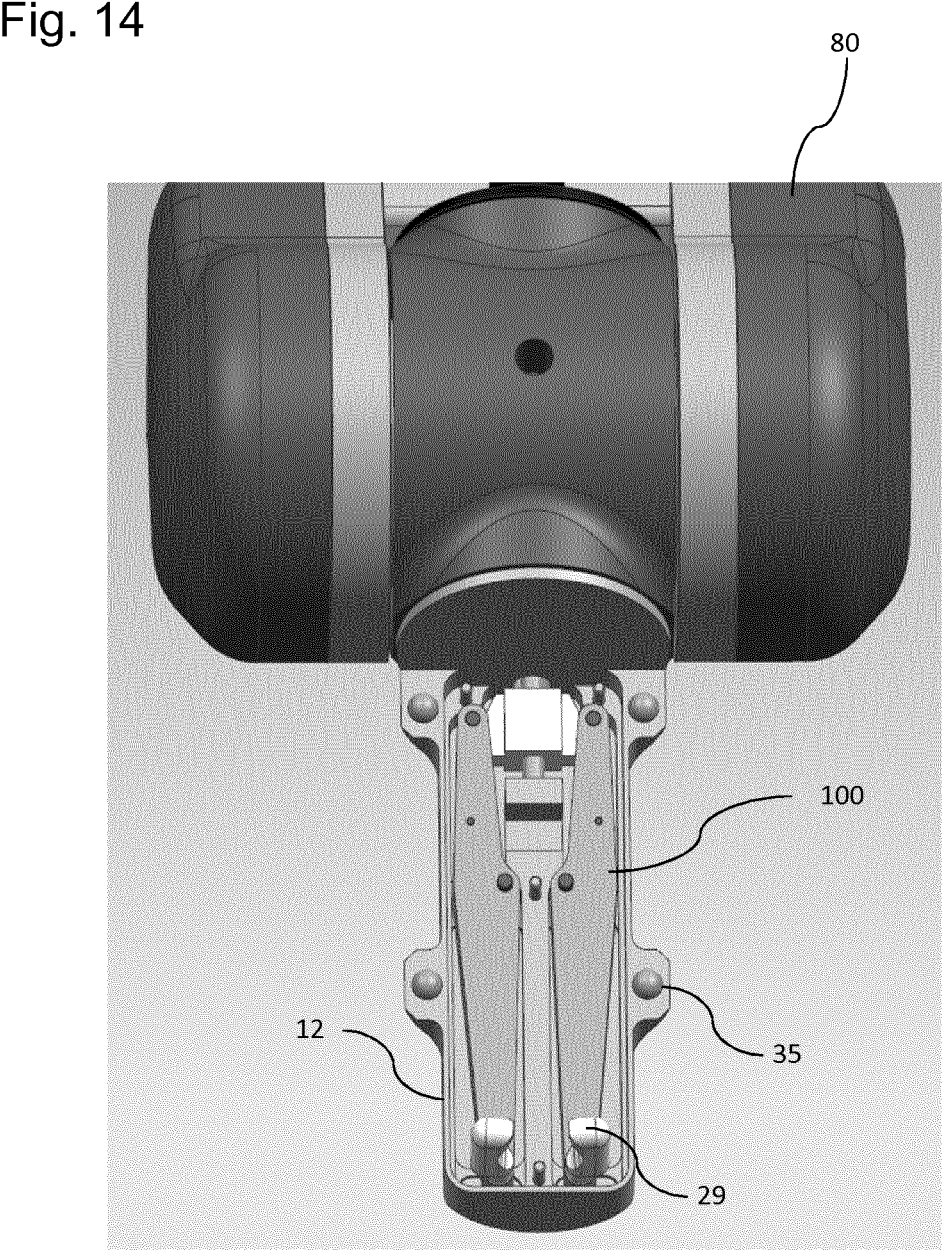
FIG. 14 is a perspective cut-out view of the second interface member according to an embodiment.
Figure 15A:
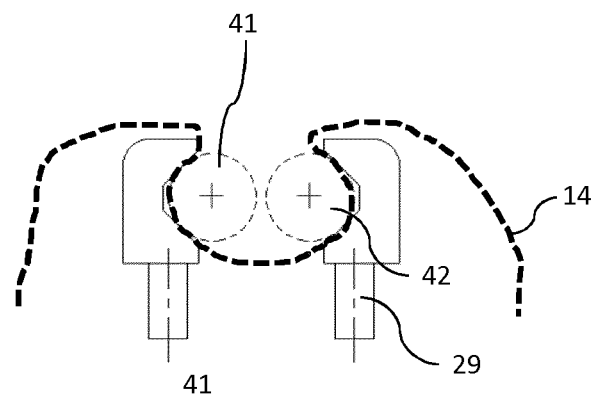
FIG. 15*a*-15*d* show some examples of the contact surfaces of the protrusions.
Figure 15B:
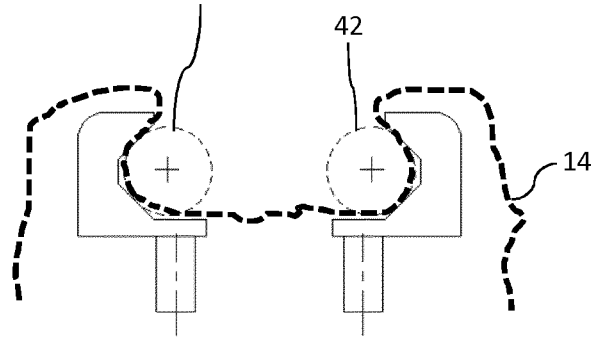
Figure 15C:
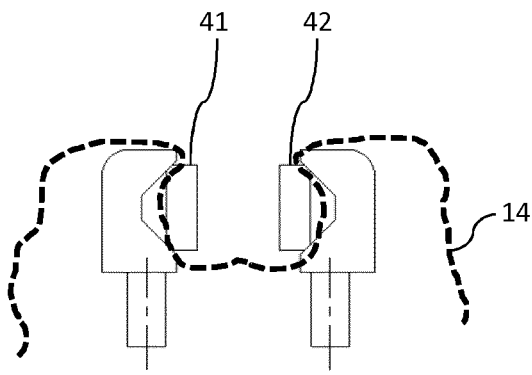
Figure 15D:
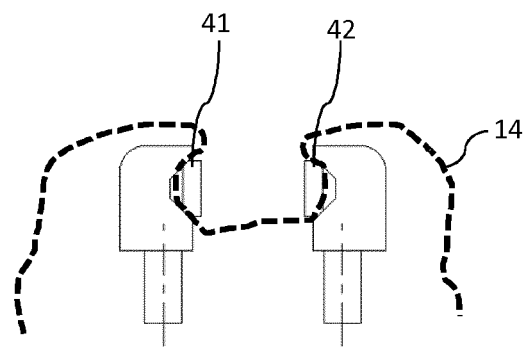

FIG. 14 is a cut-out perspective view of the first interface member 11 arranged in the robot manipulator 80 according to an embodiment. In this embodiment, the first interface member 11 contains an internal driving mechanism 100 to actuate the hinged surgical tool (not shown). The internal driving mechanism 100 symmetrically moves the two end pieces 29 that protrude through the top surface 31, see also FIG. 13A. The two end pieces 29 have opposing contact surfaces meant to be in contact with the handles 41, 42 of the surgical tool 21. FIG. 15*a*-15*d* show some examples of the contact surfaces of the protrusions 29. The contact surfaces can be v-grooved, flat, cylindrical, etc. possibly, the innermost position of the two end pieces 29 is such that the surgical tool's jaw tips are fully closed. To accommodate for different initial widths of surgical tools, different end pieces can be used, see e.g. the cross sections of FIGS. 15*a*-15*d*. It is noted that since the drape 14 is made out of a flexible material, the sterile drape 14 will not be torn due to the movement of the two protrusions 29.

The sterile draping 14 is applied such that the first interface member 11 including the protrusions 29 (also referred to as end pieces 29) are enveloped on the non-sterile side. Normally, the sterile drape 14 will be placed around the first interface member 11 and the protrusions 29 in the situation where the protrusions 29 are maximally separated.

The surgical tool 21 and second interface member 12 are sterile and can be fastened to the first interface member 11 on the sterile side of the draping 14, by couplers. The couplers may be, but is not limited to, magnetic elements, or a clamping arrangement. For example, a sterile clamping arrangement may be arranged around the first and second interface members. The clamping arrangement can be an elastic band, a tape, a string, a tie-wrap, a ring, or may include multiple parts.

Figure 13C:
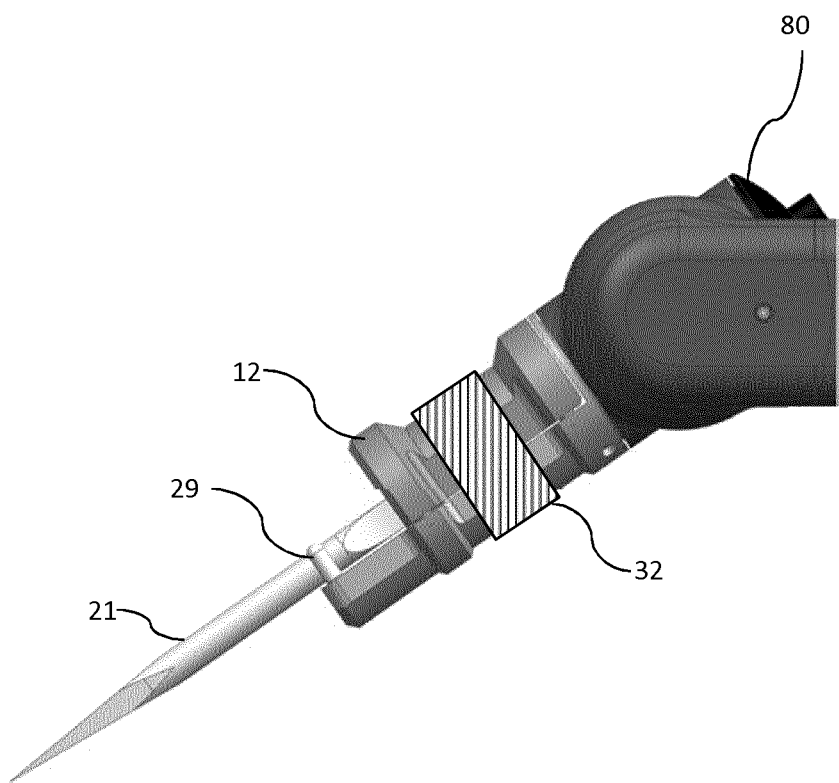
FIG. 13C shows the coupled state of the two interface members according to an embodiment.

In the embodiment of FIGS. 13A and 13B, the first interface member 11 and second interface member 12 have an external groove on their outer surface, such that when they are connected, they form a fluent grooved outer surface which is able to hold the clamping arrangement (such as a ring 32) in place, see FIG. 13C which shows the coupled state of the two interface members 11 and 12. The clamping arrangement 32 can be mounted from the front side of the surgical tool 21 and slid backwards until it reaches the groove, such that the sterile drape 14 is tightly held by the groove as well. This prevents the drape 14 from having too much slack near the operating zone. It is noted that the ring 32 may be made of a flexible material such as rubber or a flexible plastic. Alternatively, the ring 32 may be made out of two or more pieces which are coupled to each other so as to form one ring that encloses the two interface members in a clamping manner. Instead of using an clamping arrangement 32 for clamping the first and second interface members, the interface members may include magnetic elements (acting as couplers) which are arranged to attract the first second interface member 12 towards the first interface member 11. Possibly, one of the interface members includes a magnetized material while the other is made out of a ferromagnetic material.

The above described embodiments provide a solution for mounting and actuating conventional hinged surgical tools. There is no need to modify the tools before they can be mounted. All or most modifications are done in the manipulator interface members. Using unmodified conventional surgical tools has several advantages listed below:

Reliability: Conventional microsurgical tools are low tech and failure-safe;

Availability: The tools are already present in the hospital or can be purchased from standard distributors. Secondly, when not in use by the robot, the tools can be used by hand and vice versa;

Ease of use: Surgeons are already familiar with the tools;

Safety: Is a synergetic side effect of reliability, availability and ease of use. These prevent single fault conditions caused by technical, logistic and user aspects, and Cost: Operational costs are much lower for the customer, if standard microsurgical tools can be used. This includes the costs related to purchase & renewal, sterilization, maintenance, service, workflow integration, user training, and possible liabilities.

It should be noted that the above-mentioned embodiments illustrate rather than limit the presently disclosed subject matter, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. A robotic manipulator interface for coupling a hinged surgical tool to a manipulator of a surgical robot, the robotic manipulator interface comprising:
   a first interface member configured to be attached to the manipulator; and
   a second interface member attached to a flat surface of the first interface member via a coupler, the second interface member being configured to mount the hinged surgical tool,
   wherein respective contact surfaces of the first and second interface members are configured to receive an intermediate sterile drape applied to envelop the first interface member on a non-sterile side of the sterile drape,
   wherein the first interface member includes a pinching mechanism for actuating the mounted hinged surgical tool when the sterile drape envelops the first interface member and when the second interface member is coupled to the first interface member, wherein the pinching mechanism includes two movable protrusions protruding from a surface of the first interface member, the first interface member including a built-in actuating mechanism for moving the protrusions towards each other, and wherein, when the hinged surgical tool is mounted, the protrusions may be moved to push two arms of the mounted hinged surgical tool towards each other so as to actuate the mounted hinged surgical tool when the sterile drape envelops the first interface member, and
   wherein the protrusions protrude through the contact surface of the first interface member.

2. The robotic manipulator interface according to claim 1, wherein each of the protrusions includes a rounded top.

3. The robotic manipulator interface according to claim 1, wherein the surface of the first interface member is substantially flat.

4. The robotic manipulator interface according to claim 1, wherein the first interface member includes a disc shaped part and wherein the flat surface of the first interface member is one of one or multiple elongated parts extending from a front surface of the disc shaped part in a plane parallel to a main axis of the disc shaped part.

5. The robotic manipulator interface according to claim 4, wherein the first interface member is rotatable around the main axis of the disc shaped part when coupled to the manipulator.

6. The robotic manipulator interface according to claim 4, wherein the second interface member includes a substantially semi-cylindrical and a first end of the substantially semi-cylindrical body is in face sharing contact with a front surface of the disc shaped part of the first interface member.

7. The robotic manipulator interface according to claim 6, wherein the substantially semi-cylindrical body has a middle section with a cross section that is smaller than a cross section at outer ends of the semi-cylindrical body.

8. The robotic manipulator interface according to claim 4, wherein a plurality of reference spheres are arranged on the flat surface of the first interface member.

9. The robotic manipulator interface according to claim 1, wherein the second interface member includes
   an alignment element configured to be at least partly inserted in between the two arms of the mounted hinged surgical tool at a hinge point of the two arms to align the hinged surgical tool relative to the second interface member,
   a longitudinal cavity configured to accommodate at least part of the hinged surgical tool, wherein the second interface member includes an exit of the longitudinal cavity at an outer end, and
   a mounting element perpendicularly positioned relative to a main axis of the longitudinal cavity, the mounting element including a hole, an edge, or a shaped surface that is configured to match with an outer end of the hinged surgical tool, wherein the mounting element is configured to mechanically preload the hinged surgical tool against the alignment element.

10. A robotic manipulator interface according to claim 9, wherein the mounting element is flexible and/or resiliently arranged in the second interface member.

11. The robotic manipulator interface according to claim 1, wherein the first interface member and the second interface member have an external groove on their outer surface, and wherein the groove contains the coupler.

12. The robotic manipulator interface according to claim 11, wherein the coupler is a ring.

13. The robotic manipulator interface according to claim 1, wherein the coupler is on an exterior surface of the first interface member and the second interface member.

14. A surgical robot comprising a robotic manipulator interface, wherein the robotic manipulator interface comprises:
   a first interface member rotatably coupled to a manipulator of the surgical robot; and
   a second interface member which is separate from and coupleable to the first interface member, the second interface member being configured to mount a hinged surgical tool,
   wherein the first interface member includes a pinching mechanism for actuating the hinged surgical tool when the hinged surgical tool is mounted and when the second interface member is coupled to the first interface member, wherein the pinching mechanism includes two movable protrusions protruding from a surface of the first interface member, the first interface member including a built-in actuating mechanism for moving the protrusions towards each other, and wherein, when the hinged surgical tool is mounted, the protrusions may be moved to push two arms of the mounted hinged surgical tool towards each other so as to actuate the mounted hinged surgical tool, and wherein the protrusions protrude through the contact surface of the first interface member.

15. The surgical robot according to claim 14, wherein an intermediate sterile drape is applied between respective contact surfaces of the first and second interface members to envelop the first interface member on a non-sterile side of the sterile drape.

* * * * *